(12) United States Patent
Caudle

(10) Patent No.: US 6,768,576 B2
(45) Date of Patent: Jul. 27, 2004

(54) TEMPERATURE ACTUATED POSITIONING DEVICE FOR NON-LINEAR OPTICAL ELEMENTS

(75) Inventor: George Caudle, San Jose, CA (US)

(73) Assignee: Visx, Incorporated, Santa Clara, CA (US)

(*) Notice: Subject to any disclaimer, the term of this patent is extended or adjusted under 35 U.S.C. 154(b) by 110 days.

(21) Appl. No.: 10/053,513

(22) Filed: Apr. 11, 2002

(65) Prior Publication Data

US 2002/0111611 A1 Aug. 15, 2002

Related U.S. Application Data

(60) Provisional application No. 60/252,634, filed on Nov. 22, 2000.

(51) Int. Cl.$^7$ ............................. G02F 1/35; A61B 18/20
(52) U.S. Cl. .............................. 359/326; 372/21; 606/5
(58) Field of Search ................................ 359/326–332; 372/21–22; 606/5

(56) References Cited

U.S. PATENT DOCUMENTS

| | | | |
|---|---|---|---|
| 4,322,032 A | 3/1982 | Hashimoto et al. | |
| 4,536,062 A | 8/1985 | Price et al. | |
| 5,047,668 A | 9/1991 | Bosenberg | |
| 5,075,573 A | 12/1991 | Huignard et al. | |
| 5,093,832 A | 3/1992 | Bethune et al. | |
| 5,144,629 A | 9/1992 | Basu | |
| 5,168,503 A | 12/1992 | Maeda | |
| 5,272,709 A | 12/1993 | Dacquay | |
| 5,297,156 A | * 3/1994 | Deacon | 372/21 |
| 5,315,433 A | 5/1994 | Okazaki et al. | |
| 5,331,651 A | 7/1994 | Becker et al. | |
| 5,365,366 A | 11/1994 | Kafka et al. | |
| 5,416,867 A | 5/1995 | Thorsten et al. | |
| 5,446,750 A | 8/1995 | Ohtsuka et al. | |
| 5,497,387 A | 3/1996 | Okazaki | |
| 5,577,059 A | 11/1996 | Lee et al. | |
| 5,604,760 A | 2/1997 | Jang | |
| 5,657,119 A | 8/1997 | Kawasaki et al. | |
| 5,671,232 A | 9/1997 | Lee et al. | |
| 5,742,626 A | * 4/1998 | Mead et al. | 372/22 |
| 5,841,920 A | 11/1998 | Lemaire et al. | |
| 6,021,140 A | * 2/2000 | Clark et al. | 372/18 |
| 6,078,598 A | * 6/2000 | Ohtsuki et al. | 372/12 |
| 6,130,900 A | * 10/2000 | Black et al. | 372/25 |
| 6,210,401 B1 | 4/2001 | Lai | |
| 6,331,177 B1 | * 12/2001 | Munnerlyn et al. | 606/5 |
| 6,366,596 B1 | * 4/2002 | Yin et al. | 372/92 |
| 6,584,134 B2 | * 6/2003 | Yin et al. | 372/92 |

* cited by examiner

Primary Examiner—John D. Lee
(74) Attorney, Agent, or Firm—Townsend & Townsend & Crew LLP; Mark D. Barrish, Esq.

(57) ABSTRACT

Improved devices, systems, and methods use a Non-Liner Optic (NLO) to effect a conversion of an input laser energy to an output energy. The output energy will have a wavelength which is different than the input energy, and the conversion will vary in response to both an angle of the energy relative to the NLO and a temperature of the NLO. Passive control over the angle of the NLO based on thermal expansion of a member thermally coupled to the NLO can compensate for the temperature-induced change in the conversion so as to maintain a desired output frequency, conversion efficiency, phase matching, and/or the like.

9 Claims, 2 Drawing Sheets

TEMPERATURE ACTUATED POSITIONING DEVICE FOR NON-LINEAR OPTICAL ELEMENTS

This application claims the benefit of U.S. Provisional Application No. 60/252,634, filed Nov. 22, 2000.

BACKGROUND OF THE INVENTION

The present invention is generally related to devices and methods for controlling and converting laser energy wavelengths, and in a particular embodiment, provides a passive temperature compensation system for a nonlinear optic.

Lasers have been used for several years to sculpt materials into very precise shapes, excimer lasers are now widely used to ablate tissue in a variety of surgical procedures, particularly for corneal ablation during refractive surgery. The exposure of the tissue is typically controlled to produce a desired change in corneal shape. The change in corneal shape may be intended to correct a refractive error of the eye so as to eliminate the need for corrective eye glasses, or may be intended to remove a pathology from the eye.

Known laser eye procedures generally employ ultraviolet or infrared lasers to remove a microscopic layer of stromal tissue from the cornea to alter its refractive characteristics. The laser often has a frequency selected to result in photo-decomposition of the corneal tissue, preferably without causing significant thermal damage to adjacent and underlying tissues of the eye. These selected frequencies can break the radiated molecules into smaller volatile fragments photochemically by directly breaking the intermolecular bonds. These known refractive lasers often deliver laser energy as a series of discrete energy pulses, with each pulse having sufficient energy to ablate a thin volume from adjacent the corneal surface. The refractive surgical system generally control the distribution of the ablative laser energy across the cornea using, for example, ablatable masks, movable apertures, scanning systems that move the laser across the corneal surface, combinations of these techniques, and the like.

An exemplary system and method for sculpting a cornea by controlling a plurality of laser beams is described in co-pending U.S. patent application Ser. No. 09/274,499 as filed on Apr. 23, 1999, the full disclosure of which is incorporated herein by reference.

While known laser eye surgery systems have been found to be highly effective, as with all successes, still further improvements would be desirable. In particular, known laser eye surgery systems often rely on excimer lasers to produce laser energy in the deep ultraviolet wavelengths. To produce this laser energy, these excimer lasers often make use of gases such as argon-fluoride to produce a beam having a wavelength of about 193 nm. Although such excimer lasers are highly effective, there are significant maintenance costs associated with consumption of gases in the laser. Servicing costs and the lifetime of the laser chamber are less than ideal, while cleaning and replacement of the optical components is more often than would be desired.

Solid-state lasers have a number of desirable characteristics. For example, these lasers may allow higher repetition rates than excimer lasers. Solid-state lasers may also cost less and have a longer useful life than an excimer laser. Unfortunately, solid-state lasers generally do not provide highly coherent radiations in the deep ultraviolet wavelengths, which are desirable for ophthalmic surgery and for other applications including semiconductor processing, diagnostic applications, and the like.

It has previously been proposed to make use of solid-state lasers for refractive surgery and other applications by converting the laser output wavelength to a more desirable frequency using Non-Linear Optics (sometimes referred to as NLO's). Non-Linear Optics generally produce energy which is significantly different than the radiation incident thereon. Non-Linear Optics include beta barium borate, lithium triborate, cesium lithium borate, periodic pooled lithium niobate ($LiNbO_3$), and other materials such as RTA, RTP, GaAs, KTA, KTP, $LiTaO_3$, lithium tantalate, and the like. These and other nonlinear crystals can be used to convert laser energy having an initial wavelength to an alternative laser energy having a wavelength which is a harmonic of the initial wavelength, for example, by doubling a frequency of the laser energy. These and other nonlinear crystal materials may also be used to combine two or more differing laser input energies to produce an output energy of a desired wavelength, for example, by mixing the input laser energy so as to sum frequencies for the output laser energy. An exemplary method and system for producing coherent deep ultraviolet output from a solid state laser is described in U.S. Pat. No. 5,742,626 issued to Mead et al., the full disclosure of which is incorporated herein by reference.

While the frequency multiplied and sum-mixed outputs of the proposed ultraviolet solid-state laser systems provide significant potential advantages for use in laser eye surgery, semiconductor fabrication, and other uses, these proposed solid-state systems have their own disadvantages. In general, the energy conversion provided by Non-Linear Optics can vary significantly with temperature. More specifically, the angle of incidence for efficient phase matching and optical frequency conversion in a NLO may be a function of the temperature of the NLO.

In known devices in which NLO's are used to change the frequency of the laser beam, for example, second or third harmonic generation, the sum-difference mixing of two beams, or the like, the temperature of the crystal is often actively controlled so as to maintain the desired conversion characteristics. In other known systems using NLO's, the angle of incidence is actively changed by providing a control signal to a motor coupled to the NLO so as to rotate the NLO in response to sensed temperature changes. Both of these known active NLO temperature compensation systems rely on monitoring of sensor data, feeding back the sensor data to a control system, and varying the control mechanism (either temperature or angle) of the NLO so as to maintain the desired energy output. These complex feedback systems increase the complexity of the cost of the previously proposed solid-state, deep ultraviolet systems, significantly mitigating their potential advantages over more common alternatives, such a excimer lasers.

In light of the above, it would be desirable to provide improved laser systems, methods and devices. It would be particularly beneficial to provide improved techniques and systems for maintaining and/or controlling the output of NLO's, especially if these improved techniques avoided relying on active (and often expensive) feedback and control systems. The devices, systems, and methods of the present invention at least partially mitigate the disadvantages of known solid-state laser systems, and thereby realize some or all of these improvements.

SUMMARY OF THE INVENTION

The present invention generally provides improved devices, systems, and methods for converting radiant energy. The systems of the present invention generally make use of a Non-Liner Optic (NLO) to effect a conversion of an input laser energy to an output energy. The output energy will often have a wavelength which is different than the input energy. The conversion provided by the NLO will often vary in response to both an angle of the energy relative to the NLO, and in response to a temperature of the NLO. The present invention generally provides passive control over the angle of the NLO based on thermal expansion of a member which is thermally coupled to the NLO. Advantageously, the thermal-expansion induced change in angle of the NLO can compensate for the temperature-induced change in the conversion so as to maintain a desired output frequency, conversion efficiency, phase matching, and/or the like.

In a first aspect, the invention provides a laser system comprising a laser generating a laser beam with a first frequency. A NLO is disposed in an optical path of the beam. The NLO effects a conversion of the first frequency to a second frequency. The conversion varies with an angle of the NLO relative to the optical path. A first member has a first thermal coefficient of expansion and is thermally coupled to the NLO so that a change in a dimension of the first member with a change in temperature of the NLO effects a change in the angle of the NLO.

Preferably, the change in dimension of the member effects a predetermined change in the angle of the NLO so as to effect a desired adjustment in the conversion. Typically, the angle-induced adjustment in conversion will compensate for temperature-induced changes in the conversion. The NLO will often pivot within the optical path in response to the passive expansion by the member so that the second frequency remains within a desired (often predetermined) range when a temperature of the NLO varies throughout a predetermined temperature range during operation of the laser system.

In the exemplary embodiment, first and second members having differing coefficients of thermal-expansion are attached together. Differing thermal expansion of the attached members alters a bend angle of the members, and the bend angle pivots the NLO within the optical path. Optionally, an angle adjustment mechanism may allow varying of the NLO angle independent of temperature for calibration and adjustment of the system. Suitable adjustment mechanisms may make use of structures similar to micrometer linear scale systems.

In another aspect, the invention provides a laser eye surgery system comprising a laser generating a laser beam with a first frequency. A NLO is disposed in an optical path of the beam so as to define an angle relative to the beam. The NLO effects a conversion of the first frequency to a second frequency. The conversion exhibits an angle-induced change with a change in the angle, and a temperature-induced change with a change in a temperature of the NLO. A compensator includes a first member having a thermal coefficient of expansion. The first member is thermally coupled to the NLO so that the change in temperature of the NLO effects a change in a dimension of the first member. The first member is mechanically coupled to the NLO. The change in dimension of the first member effects the change in angle of the NLO so that the angle-induced change in the conversion compensates for the temperature-induced change in the conversion. A beam directing system is disposed in the optical path from the NLO. The beam directing system selectively directs the beam toward portions of a cornea so as to effect a desired change in a refractive characteristic of the cornea.

In a method aspect, the invention provides a method comprising generating a laser beam at a first frequency with a laser. The laser beam is converted to a second frequency with a NLO. The converting step varies with a temperature of the NLO, and with an angle defined by the NLO and the laser beam. Temperature-induced variations in the NLO are passively compensated for by transferring heat to a member from the NLO. Thermal expansion of the member resulting from the transfer of heat adjusts the angle of the NLO.

DESCRIPTION OF THE SPECIFIC EMBODIMENTS

Figure 1:
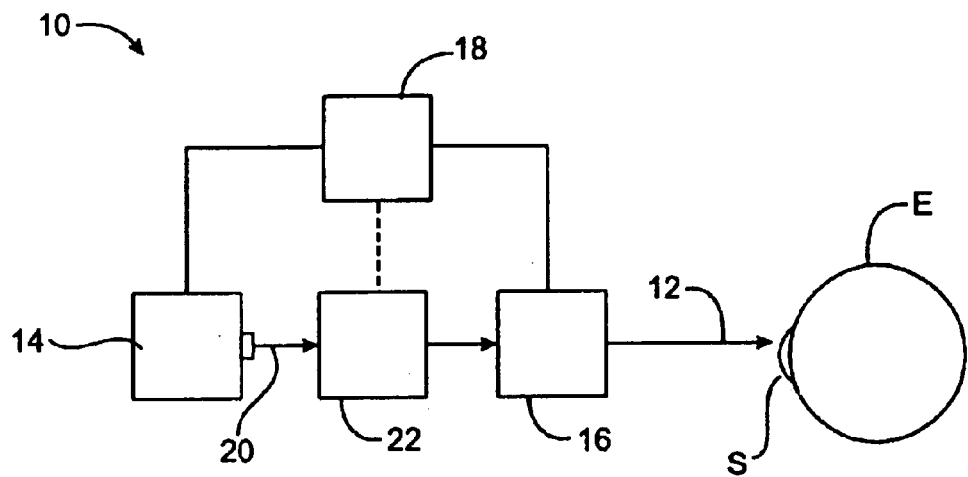
FIG. 1 schematically illustrates a laser eye surgery system and method according to the principles of the present invention.

Referring now to FIG. 1, a refractive surgery system 10 selectively directs laser energy 12 onto a corneal surface S of eye E. As is well described in the patent literature, surface S may be a surface of a stromal tissue. This stromal tissue may be exposed by removing an overlying epithelial layer of the cornea by laser ablation, scrapping, abrasion, or the like. In many cases, the surface S of the stromal tissue will be exposed by selectively incising the cornea and displacing a portion or "flap" of the corneal tissue while the flap remains attached outside the visually used portion of the cornea, in a procedure referred to as laser in situ keratomileusis (LASIK).

Laser system 10 generally includes a laser 14 and a beam directing system 16, both of which are coupled to a controller 18. Controller 18 will typically comprise a processor such as a PC workstation including a program stored on a tangible medium so as to selectively direct laser energy 12 onto surface S of the cornea.

Directing system 16 will often selectively profile and/or deflect laser energy 12 laterally over the surface S of the cornea. Systems which laterally deflect laser energy 12 (using, for example, deflectable mirrors, prisms, variable offset imaging lenses, or the like) are sometimes referred to as scanning systems. Some known laser eye surgery systems selectively block a portion of the laser energy in some or all of the pulses of laser energy 12 (using, for example, variable apertures such as a variable iris and/or a variable width slit, an ablatable mask, or the like) so that the pattern of laser energy striking surface S effects the desired resculpting. In some systems, a combination of profiling and scanning are used. Commercial laser systems including exemplary energy directing systems and their associated controllers are available from VISX of Santa Clara, Calif., SUMMIT TECHNOLOGY of Massachusetts, NIDEK Co., LTD. of Gamagori, Japan, and others.

Controller 18 is also coupled to laser 14 so as to control firing of the laser. While laser energy 12 will typically comprise pulses of laser energy suitable for photodecomposition of corneal tissue, preferably having a wavelength and a range from about 180 nm to about 210 nm, and ideally having a wavelength of about 193 nm, the initial laser energy 20 generated by laser 14 may have a very different wavelength.

Laser 14 will generally comprise a solid-state laser, often comprising a diode pumped Nd:yAG laser producing a beam having a wavelength of about 1 micron. Alternative solid-state lasers may include many alternative materials known in the art. An exemplary laser is more fully defined in U.S. Pat. No. 5,742,626 the full disclosure of which has previously been incorporated by reference.

Laser system 10 also includes a frequency conversion system 22 in an optical path of the laser energy from laser 14. Frequency conversion system 22 converts a wavelength of initial laser energy 20 to a safe photoablative wavelength. To change the wavelength of the laser energy to the desired photoablation wavelength, frequency conversion system 22 may include one or more non-linear optics, the frequency conversion system 22 typically including a plurality of non-linear optics. Each non-linear optic will convert one or more input frequencies to an alternative frequency, with the overall conversion from the initial laser energy 20 to the ablative energy 12 often occurring as a series of discreet steps.

Figure 2:
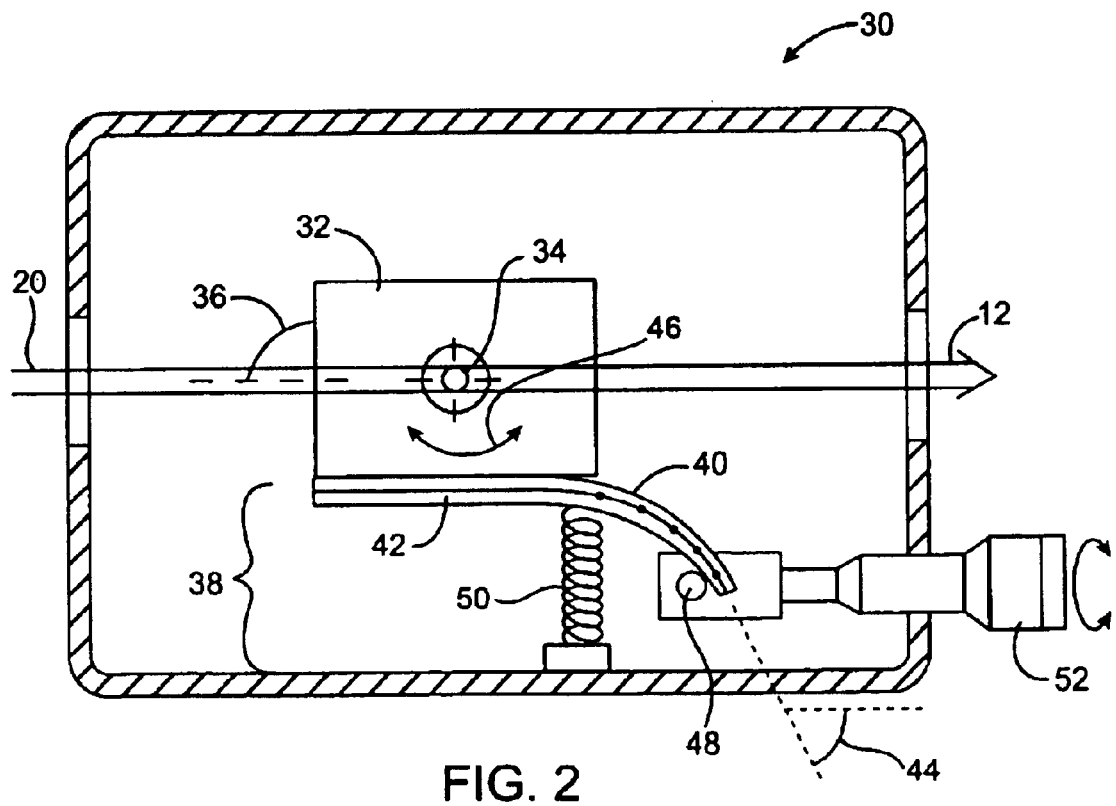
FIG. 2 is partial cross-sectional view showing a Non-Linear Optic (NLO) for converting a frequency of a laser beam and a support system supporting the NLO so that a change in temperature of the NLO varies an angle of the NLO relative to the laser beam.

To reduce the sensitivity of laser system 10 to changes in temperature, one or more of the non-linear optics will generally be passively positioned within the optical path using a temperature actuated positioning device 30 as illustrated in FIG. 2.

Referring now to FIG. 2, temperature actuated positioning device 30 selectively pivots a non-linear optic 32 about a pivotal support 34 so as to vary an angle 36 defined by the non-linear optic and laser beam 20.

Angle 36 will typically comprise an angle of incidence of initial laser energy 20 upon a surface of non-linear optic 32. The desired angle of incidence for efficient phase matching and optical frequency conversion for non-linear optic 32 varies as a function of a temperature of the non-linear optic. As laser energy 20 can be quite significant, and as the non-linear optic does not have perfect conversion efficiency, laser energy 20 can significantly heat non-linear optic 32, so that a temperature of the non-linear optic may vary considerably during operation of laser system 10.

To passively compensate for changes in the temperature of non-linear optic 32 by adjusting angle 36, positioning device 30 includes a compensator 38 thermally coupled to non-linear optic 32. Compensator 38 includes first and second members 40,42 attached to non-linear optic 32 so that the temperatures of the members vary with temperature of the non-linear optic. First and second members 40, 42 flex resiliently, and are attached together so as to define a bend angle 44. The members will generally comprise differing materials having differing thermal coefficients of expansion, so that angle 44 will vary with a temperature of the members (and hence with a temperature of non-linear optic 32).

First and second members 40, 42 generally together define a bimetallic strip, with the two differing metals being affixed together by any of a variety of attachment structures, including welds, spot-welds, fasteners, adhesives, and the like.

Suitable materials for fabricating members 40, 42 include stainless steel, KOVAR™, metals, brass, copper, and the like. Members 40, 42 may alternatively comprise non-metallic materials including polymers, composite materials, and the like.

Optionally, first member 40 may have a thermal coefficient of expansion which is significantly greater than the thermal coefficient of expansion of second member 42. When a temperature of non-linear optic 32 increases, a length of first member 40 will increase to a greater extent than a length of second member 42. As a result of this differential thermal expansion, bend angle 44 will increase. It should be noted that in some embodiments, second member 42 may have a greater thermal coefficient of expansion than first member 40, and/or that one or both of the members may comprise materials having a negative thermal coefficient of expansion.

As bend angle 44 changes, varying deflection of first and second members 40, 42 cause non-linear optic 32 to pivot about pivotal support 34 as indicated by arrows 46. More specifically, the deflecting first and/or second members 40, 42 are urged against an adjustable pin 48 by a biasing systems 50. The first and/or second members 40, 42 ride against pin 48, and as the members are attached along non-linear optic 32, changes in the bend angle cause the non-linear optic to pivot.

Adjustable pin 48 is supported by an adjustment mechanism 52. Adjustment mechanism 52 includes a precise linear (and/or angle) adjustment drive similar to a micrometer drive. Adjustment of the micrometer drive adjustment mechanism varies the locations of the contact interface between pin 48 and first and/or second members 40, 42 to calibrate the pivotal angle of the non-linear optic.

It should be understood that temperature actuated positioning device 30 is only one example of a mechanism in which thermal expansion effects a change in a position of a non-linear optic so as to compensate for temperature-induced changes in the characteristics of the non-linear optic. Alternative temperature compensation packages which might be modified for use with non-linear optics within the scope of the present invention are also possible. A more detailed schematic illustration of an exemplary solid-state laser system 10' is shown-in FIG. 3. Systems 10' again includes a laser 14 generating an initial laser beam 20, with the laser optionally comprising a 40 WATT diode pumped Nd:yAG laser which is Q-switched and cavity-dumped to provide a short pulse at 10 Kh repetition rates. This exemplary laser is capable of producing a beam having a wavelength of about 1.065 microns.

Figure 3:
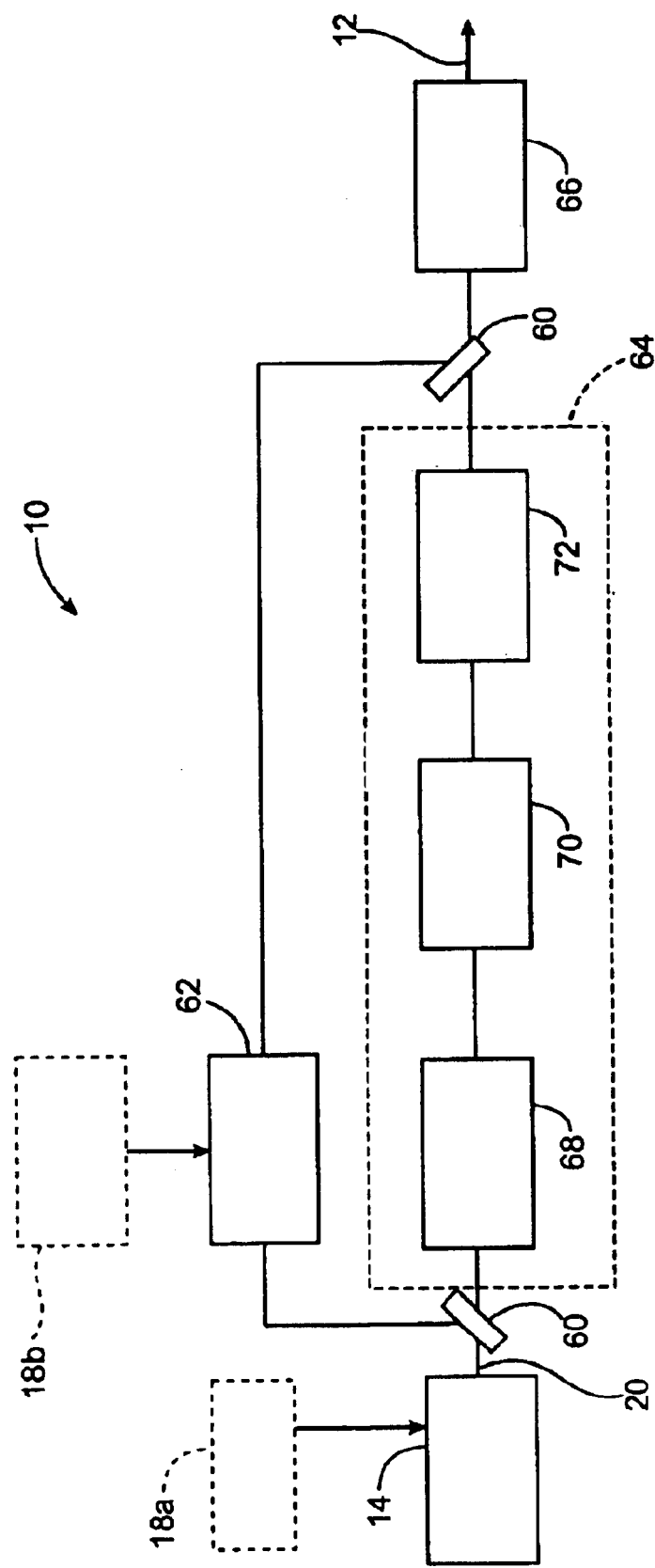
FIG. 3 schematically illustrates an exemplary solid-state laser system including a plurality of temperature actuated positioning systems for an associated plurality of non-linear optical elements.

Initial beam 20 is split by a beam splitter 60 which passes a portion of a portion of the beam to an optical parametric oscillator 62 and alternative portion of the beam to a harmonic generation stage 64. These two beam portions are combined in a sum-frequency generator 66 to generate the desired ultraviolet wavelength beam 12. Harmonic generation stage 18 includes a number of non-linear optics, including a frequency doubler 68, a fourth harmonic generator 70, and a fifth harmonic generator 72. The structure in use of each of these components is described more fully in U.S. Pat. No. 5,742,626 which has previously been incorporated by reference. As illustrated in FIG. 3, the components will optionally be coupled to separate control modules 18A, 18B, with the control modules optionally running on a single processor or a plurality of separate processor boards.

In general, the non-linear optics of exemplary laser system 10' will be coupled to positioning devices 30 as described above with reference to FIG. 2, so as to avoid and/or decrease reliance of the solid-state laser system on active control of the position and/or temperature of the non-linear optics using sensor actuated motors, thermal control systems, and the like. While such active control systems may be used in conjunction with the passive, thermally activated positioning system described herein, it may be possible to decrease and/or eliminate some or all of the active controls for the non-linear optical elements for multi-component solid-state laser systems, such as that illustrated in FIG. 3.

While the exemplary of the present invention has been described has been described in some detail by way of example, and for clarity of understanding a variety of modifications, changes, and adaptations will be obvious to those of skill in the art. Hence the scope of the present invention is limited solely by the appended claims.

What is claimed is:

1. A laser system comprising:

a laser generating a laser beam with a first frequency;

a non-linear optic disposed in an optical path of the beam, the non-linear optic effecting a conversion of the first frequency to a second frequency, the conversion varying with an angle of the non-linear optic relative to the optical path; and a first member having a first thermal coefficient of expansion, the first member thermally coupled to the non-linear optic so that thermal expansion in a dimension of the first member with a change in temperature of the non-linear optic effects a change in the angle of the non-linear optic.

2. The laser system of claim 1, wherein the thermal expansion of the member effects a predetermined change in the angle of the non-linear optic when the non-linear optic undergoes the change in temperature, and wherein the predetermined change in the angle effects a desired adjustment in the conversion.

3. The laser system of claim 2, wherein the conversion provided by the non-linear optic also varies with a temperature of the non-linear optic, and wherein the angle-induced adjustment in the conversion compensates for temperature-induced changes in the conversion by the non-linear optic.

4. The laser system of claim 3, wherein the non-linear optic is pivoted by the member within the optical path so that the second frequency remains within a desired range when a temperature of the non-linear optic varies throughout a predetermined temperature range during operation of the laser system.

5. The laser system of claim 1, further comprising a second member attached to the first member, the second member having a second coefficient of thermal expansion, the second expansion coefficient being different than the first expansion coefficient, wherein differential thermal expansion alters a bend angle of the attached first and second members, the angle of the non-linear optic being mechanically coupled to the bend angle.

6. The laser system of claim 1, further comprising a beam control system for selectively directing the beam onto a cornea of a patient so as to effect a desired refractive change, the laser system comprising a laser eye surgery system.

7. The laser system of claim 6, wherein the laser comprises a solid-state laser, and wherein a frequency of the beam incident on the cornea is in a range from about 180 to about 210 nm.

8. A laser eye surgery system comprising:

a laser generating a laser beam with a first frequency;

a non-linear optic disposed in an optical path of the beam so as to define an angle relative to the beam, the non-linear optic effecting a conversion of the first frequency to a second frequency, wherein the conversion has an angle-induced change in with a change in the angle, and wherein the conversion has a temperature-induced change with a change in a temperature of the non-linear optic;

a compensator including a first member having a thermal coefficient of expansion, the first member thermally coupled to the non-linear optic so that the change in temperature of the non-linear optic effects a change in a dimension of the first member, the first member mechanically coupled to the non-linear optic, the change in dimension of the first member effecting the change in angle of the non-linear optic so that the angle-induced change in the conversion compensates for the temperature-induced change in the conversion; and a beam directing system in the optical path from the non-linear optic, the beam directing system selectively directing the beam toward portions of a cornea so as to effect a desired change in a refractive characteristic of the cornea.

9. A method comprising:

generating a laser beam at a first frequency with a laser;

converting the beam to a second frequency with a non-linear optic, wherein the converting step varies with a temperature of the non-linear optic and with an angle defined by the non-linear optic and the laser beam;

passively compensating for temperature-induced variations in the non-linear optic by transferring heat to a member from the non-linear optic so that thermal expansion of the member adjusts the angle of the non-linear optic.

* * * * *